(12) United States Patent
Brown et al.

(10) Patent No.: US 6,255,954 B1
(45) Date of Patent: Jul. 3, 2001

(54) DETECTION OF WEAR-PARTICLES AND OTHER IMPURITIES IN INDUSTRIAL OR OTHER FLUIDS

(75) Inventors: Robert W. Brown, Solon; Yu-Chung Norman Cheng, Richmond Heights; William C. Condit, Strongsville; Donald E. Schuele, Lyndhurst, all of OH (US)

(73) Assignee: Reid Asset Management Company, Willoughby, OH (US)

( * ) Notice: Subject to any disclaimer, the term of this patent is extended or adjusted under 35 U.S.C. 154(b) by 0 days.

(21) Appl. No.: 09/317,506

(22) Filed: May 24, 1999

Related U.S. Application Data
(60) Provisional application No. 60/117,889, filed on Jan. 29, 1999.

(51) Int. Cl.[7] ................................................. G08B 21/00
(52) U.S. Cl. ........................ 340/603; 340/631; 324/698; 73/304 R
(58) Field of Search ................................... 340/603, 631, 340/627, 620; 324/689, 663, 698, 438, 711, 53.04; 73/61.43, 53.01, 54.01, 304 R, 152.39; 205/83; 204/421

(56) References Cited

U.S. PATENT DOCUMENTS

| | | |
|---|---|---|
| 4,030,028 | 6/1977 | Allender .................................. 324/65 |
| 4,392,110 | 7/1983 | El-Menshawy et al. ............. 324/453 |
| 4,646,070 * | 2/1987 | Yasuhara ............................. 340/603 |
| 4,675,662 * | 6/1987 | Dondo ................................. 340/603 |
| 4,686,857 * | 8/1987 | Kato ................................... 73/304 R |
| 4,764,258 * | 8/1988 | Kauffman ............................ 201/1 T |
| 5,274,335 * | 12/1993 | Wang .................................. 324/689 |
| 5,457,396 | 10/1995 | Mori et al. .......................... 324/724 |
| 5,696,331 | 12/1997 | Otsuka et al. ...................... 73/865.8 |

FOREIGN PATENT DOCUMENTS
2110783   10/1998 (RU).

OTHER PUBLICATIONS
International Search Report dated Oct. 10, 2000 for Application No. PCT/US00/14395.

* cited by examiner

*Primary Examiner*—Jeffery Hofsass
*Assistant Examiner*—Anh La
(74) *Attorney, Agent, or Firm*—Renner, Otto, Boisselle & Sklar, LLP (57) ABSTRACT

The present invention includes a method of detecting contamination in a fluid sample includes bringing a fluid sample into contact with a pair of spaced apart electrodes and applying a plurality of voltages across the electrodes, wherein the plurality of voltages vary in magnitude between a first and second voltage level. The current is then measured between the electrodes at the plurality of voltages and a contamination level is determined using the measured currents. The present invention also includes a system for determining a particulate contamination level in a fluid sample. The system includes a sensor including a pair of spaced apart electrodes, wherein the fluid sample is brought into contact with the electrodes for detection of the level of particulate contamination therein, and a voltage application means for applying a voltage across the spaced apart electrodes. The system also further includes a current sensor coupled to one of the electrodes. The current sensor measures a current magnitude between the electrodes and the current magnitude is associated with the particulate contamination level in the fluid sample.

32 Claims, 5 Drawing Sheets

DETECTION OF WEAR-PARTICLES AND OTHER IMPURITIES IN INDUSTRIAL OR OTHER FLUIDS

This application is a provisional of 60/117,889, filed Jan. 29, 1999.

FIELD OF THE INVENTION

The present invention relates generally to an apparatus and method for analyzing fluids such as lubricants. More particularly, the invention relates to a system and method for detecting particulate or wear-particle contamination levels in a fluid.

BACKGROUND OF THE INVENTION

The presence of corrosive products, contaminants, metallic particles, oxidation, etc., in fluids such as lubricants can cause problems. For example, contaminants in lubricants can lead to damage of machinery in which the lubricant is utilized, causing unnecessary or accelerated wear on the lubricated members.

Various approaches have been developed to detect conditions such as deterioration or contaminants in fluids. One conventional system described in U.S. Pat. No. 4,646,070 utilizes a pair of capacitor electrodes positioned in a fluid. The fluid serves as a dielectric between the electrodes to develop an AC voltage response across the capacitor electrodes. Based on the response, the deterioration of the fluid is determined. This solution suffers from a drawback because the sensor is large and bulky and is difficult to move from machine to machine to make fluid contamination measurements.

U.S. Pat. No. 5,262,732 describes a system which utilizes an oscillator circuit coupled to a capacitive sensor. The fluid under test is placed in a reservoir containing the capacitive sensor and the oscillator circuit generates a signal having a frequency that increases or decreases depending on the capacitance of the sensor. The system of U.S. Pat. No. 5,262,732 is also rather large and cumbersome and does not lend itself to portability. In the field, it would be difficult to transport the device from machine to machine to analyze the lubricant at the location of the machinery, for example.

Figure 1A:
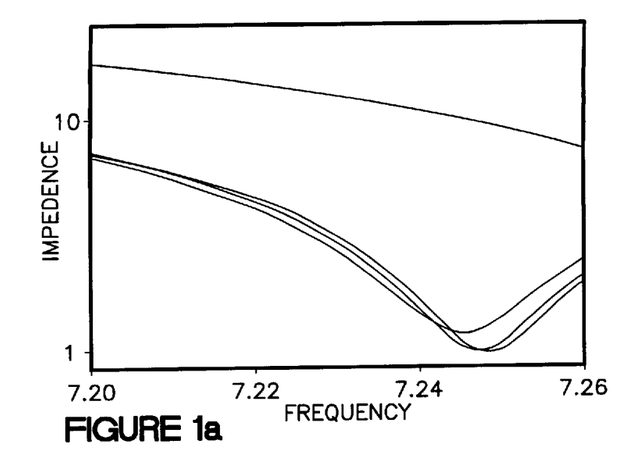
FIG. 1a is a graph illustrating how the magnitude of the complex impedance of fluid samples having differing types of contamination vary over frequency in a capacitive electrode type sensor.
Figure 1B:
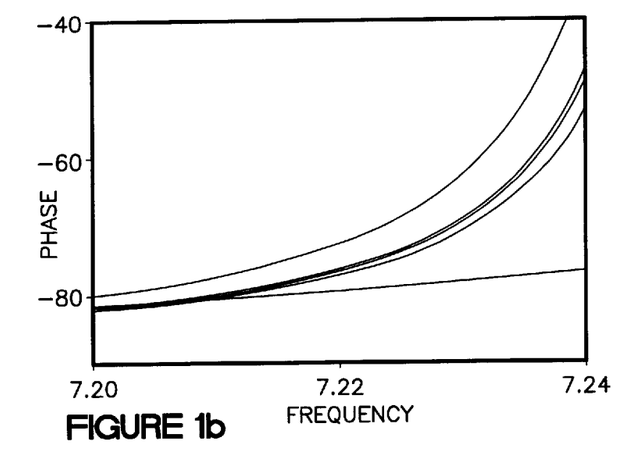
FIG. 1b is a graph illustrating how the phase of the complex impedance of fluid samples having differing types of contamination vary over frequency in a capacitive electrode type sensor.

Another type of portable sensor is based on impedance spectroscopy. An impedance spectroscopy system includes capacitor electrodes which are modeled as a complex impedance having an effective capacitor in parallel with an effective resistor. The fluid sample is placed over the capacitor electrodes and forms the dielectric therebetween. The magnitude and phase of the system impedance are then measured at a plurality of different frequencies, and by analyzing the magnitude and phase of the impedance over the frequency range, changes in the permittivity and conductivity of the fluid sample are identified and used to identify the type and level of fluid contamination. The manner in which the complex impedance (magnitude and phase) is used over a range of frequencies to identify various types of fluid contamination can be seen in prior art FIGS. 1a and 1b.

For example, at low frequencies, the reactance of the effective capacitor is large and current will flow primarily through the effective resistor. Thus a low frequency impedance reading provides information regarding the conductivity of the fluid and thus can be used to provide information about the presence of water as a contaminant in the fluid sample. At higher frequencies, the reactance of the effective capacitor is less than at low frequencies and more current will thus flow through the effective capacitor. Therefore at higher frequencies, the measured impedance (magnitude and phase) provides more information about the permittivity of the fluid. The high frequency information thus can provide information about the effects of wear debris and oxidation on the fluid sample.

Metallic particulate contaminants from machine wear and lubricant deterioration due to oxidation may be detected more readily through a higher range of frequencies by indirectly evaluating the permittivity of the fluid because the permittivity of a fluid describes how the fluid responds in an electric field. For example, when a fluid breaks down, experiencing oxidation, it is hypothesized that the hydrocarbon chains in the molecular structure split and form polar dipoles. Therefore, under the influence of an electric field, the dipoles will become oriented in the direction of the electric field. When the electric field changes its direction, the dipoles also re-orient themselves with the changing field. As the frequency escalates, it becomes more difficult for the dipoles to keep pace with the field variations. The maximum frequency at which the dipoles can keep up with the changing electric fields is called the relaxation frequency. At frequencies greater than the relaxation frequency the dipole alignment with the changing electric field lags, causing a drop off in the phase of the complex impedance. In this manner, one may indirectly evaluate the permittivity of the fluid by measuring the complex impedance of the fluid across the frequency range. Ferromagnetic particulates may also be detected more readily at a higher range of frequencies due to their behavior in electric fields.

Although the above impedance spectroscopy provides a good technique for identifying various forms of fluid contamination, the prior art devices do not provide sufficient sensitivity to reliably identify contamination levels below, for example, about 100 ppm. In view of the foregoing, it is an object of the present invention to improve the fluid contamination sensitivity over the prior art systems and methods.

SUMMARY OF THE INVENTION

The present invention relates to a system and method of determining a particulate or wear-particle contamination level in fluids using an electrogravity phenomena.

According to one aspect of the present invention, a method of detecting contamination in a fluid sample is disclosed. A fluid sample is brought into contact with a pair of spaced apart electrodes and a voltage is applied across the electrodes. A current between the electrodes is then measured and based on the measured current, a determination is made whether a predetermined contamination level exists within the fluid sample.

According to another aspect of the present invention, a method for determining a particulate contamination level in a fluid sample is disclosed. The method includes bringing a fluid sample into contact with a pair of spaced apart electrodes. A plurality of different voltages is then applied across the electrodes and the current through the electrodes is measured at each of the applied voltages to generate an I/V curve. Using the I/V curve or simply the measured current magnitude, the contamination level of the fluid sample is determined, for example, by identifying the voltage at which the current exceeds a predetermined threshold and correlating the identified voltage to the contamination level.

According to yet another aspect of the present invention, an electrogravity phenomena has been discovered and utilized to identify a particulate or wear-particle contamination level within a fluid sample. By applying a voltage across a pair of electrodes which are immersed in the fluid sample, an electric field forms between the electrodes and the particulate contaminants within the fluid sample are influenced by gravity and the electric field. As the voltage across the electrodes is increased, a critical voltage is reached and some of the contaminants form a bridge between the electrodes, causing an increase in current between the electrodes. It has been found that the value of the critical voltage is related to the particulate or wear-particle concentration level in the fluid sample. In particular, it has been found that lower concentrations of contaminants in the fluid correspond to high critical voltages while in similar circumstances a high concentration of contaminants in a fluid corresponds to lower critical voltages. Use of the electrogravity phenomena provides increased detection sensitivity over prior art methods, allowing detection of particulate concentration levels of less then 100 ppm.

According to still another aspect of the present invention, a system for determining a particulate contamination level in a fluid sample is disclosed. The system includes a sensor having at least two spaced apart electrodes which is immersed in a fluid sample. A voltage application circuit, for example, a variable power supply, is applied across the electrodes and a current sensor is coupled to one of the electrodes. As various voltages are applied across the electrodes, the current sensor measures the current magnitude between the electrodes. The measured currents are then used, preferably using a processor, to identify a critical voltage at which the current between the electrodes exceeds a predetermined threshold or increases faster than a predetermined rate. The identified critical voltage is then used to determine the particulate contamination concentration level.

To the accomplishment of the foregoing and related ends, the invention comprises the features hereinafter fully described and particularly pointed out in the claims. The following description and drawings set forth in detail certain illustrative embodiments of the invention. These embodiments are indicative, however, of merely a few of the various ways in which the principles of the invention may be employed. Other objects and advantages of the invention will become apparent from the following detailed description of the invention when considered in conjunction with the drawings.

BRIEF DESCRIPTION OF THE DRAWINGS

FIG. 3a is a perspective view of electric field lines associated with a capacitive electrode type sensor having a voltage applied across the electrodes;

FIG. 3b is a cross section view of FIG. 3a;

FIG. 3c is a plan view illustrating a substrate, wherein the electrodes are interdigitated;

DETAILED DESCRIPTION OF THE INVENTION

The present invention will now be described with reference to the drawings wherein like reference numerals are used to refer to like elements throughout. The present invention relates to a system and method of determining a particulate or wear-particle contamination level in a fluid sample. The present invention utilizes a newly discovered electrogravity phenomena to detect the particulate contamination level of a sample fluid with a high degree of sensitivity, for example, detecting contamination levels below 100 ppm.

It has been discovered by the inventors of the present invention that if a pair of spaced apart electrodes are placed in a fluid sample and a voltage is applied across the electrodes which is increased over time, a critical voltage will be reached at which point a current through the electrodes will markedly increase. The critical voltage has been found to correlate to a particulate or wear-particle contamination level in the fluid sample and thus allows the particulate or wear-particle contamination level to be identified with a high degree of accuracy and sensitivity. The increase in current between the electrodes at the critical voltage is due to particulates within the fluid forming a bridge between the electrodes due to the influence of gravity and the electric field lines between the electrodes caused by the applied voltage. A detailed discussion of the above electrogravity phenomena follows below.

Figure 2:
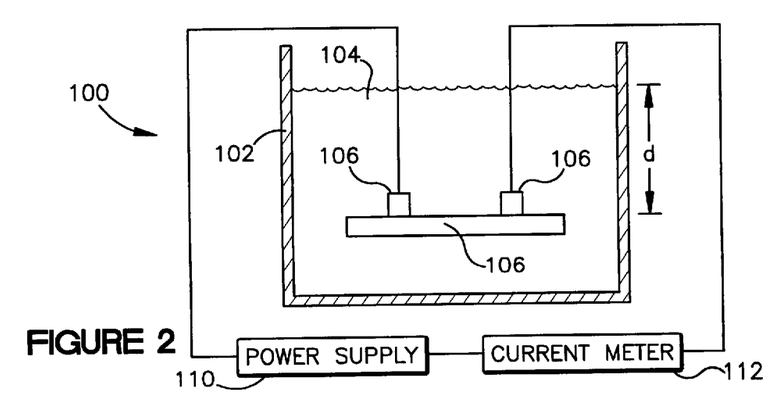
FIG. 2 is a diagram illustrating an experimental test set-up for identifying an electrogravity phenomena associated with particulate contamination in a fluid sample according to the present invention.

FIG. 2 is a diagram illustrating an experimental test set-up 100 for demonstrating the electrogravity phenomena according to the present invention. The test set-up 100 includes a container 102, for example, a 50 mL beaker, containing a fluid sample 104, for example, an oil lubricant containing ferrous particulate contaminants (i.e., wear-particles). A pair of electrodes 106 having a spacing therebetween, for example, about 7–12 mils reside on a substrate 108, which is immersed in the fluid sample 104. A power supply 110 is then connected across the electrodes with a current meter 112 connected in series therewith as shown. The substrate 108 preferably is immersed within the fluid 104 to a predetermined depth "d" as illustrated.

Figures 3A, 3B, 3C:
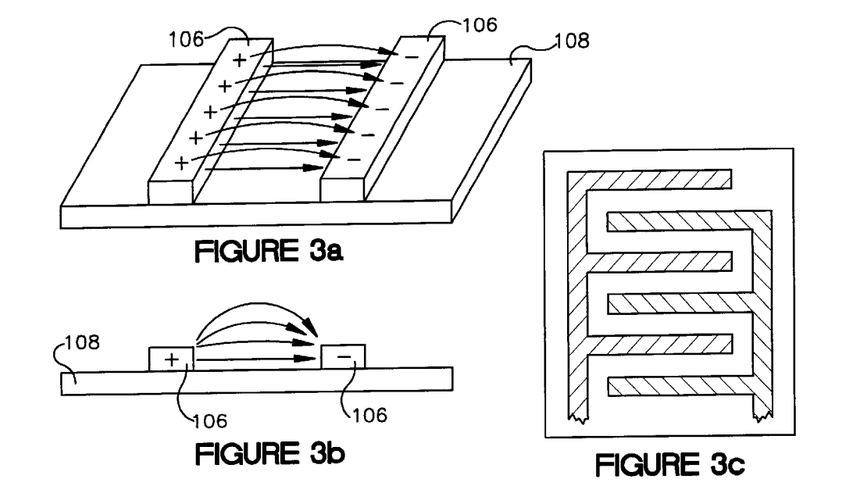

After a predetermined time is allowed to lapse following the introduction of the fluid 104 into the container 102 (i.e., a settling time), for example, about 20 seconds, the power supply 110 is activated and applies an initial voltage across the electrodes 106 (e.g., 0–10 volts). The application of a voltage across the electrodes 106 causes an electric field to develop between the electrodes, wherein the electric field strength is a function of the value of the applied voltage and the electrode spacing. The electric field between the electrodes 106 can be represented graphically as electric field lines, as illustrated in FIGS. 3a and 3b. The electric field lines help illustrate the strength and directionality of the electric field between the electrodes 106 and thus the forces which are exerted on the wear-particles in the fluid as gravity pulls the wear-particles in the fluid 104 above the electrodes 106 down toward the electrodes 106. Note that although a single pair of electrodes may be utilized as in FIGS. 2, 3a and 3b, the electrodes may interdigitated, as illustrated in FIG. 3c.

Gravity acts upon the wear-particles and exerts a downward force thereon during the settling time. At the same time, the electric field between the electrodes 106 also exerts a force on the wear-particles and tends to accumulate the wear-particles along the electric field lines (i.e., causing some of the wear-particles to align). For small applied voltage values, the electric field is not sufficiently strong to fully align the wear-particles together between the electrodes 106 and the current which is measured flowing between the electrodes 106 is relatively low (that is, the current through the electrodes 106 is a function of the conductivity of the fluid sample).

As the applied voltage across the electrodes 106 from the power supply 110 is increased, the electric field intensity grows and at some critical value (i.e., the critical voltage), the electric field intensity is sufficiently strong to cause various wear-particles in the fluid sample 104 to form a bridge between the electrodes 106, thereby reducing substantially the resistance between the electrodes (e.g., from about 10 MΩ or more to about 100 Ω or less). The reduced resistance between the electrodes 106 causes the current through the electrodes to increase markedly in accordance with Ohm's law.

Figure 4A:
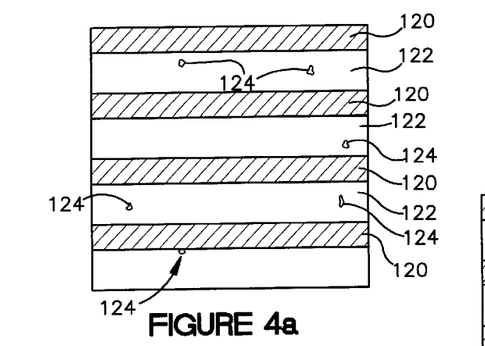
FIGS. 4a–4c are amplified plan views of capacitive electrodes having differing voltage values applied thereto, and illustrating the formation of particulate bridging between the electrodes as the applied voltage value is increased according to the present invention.
Figure 4B:
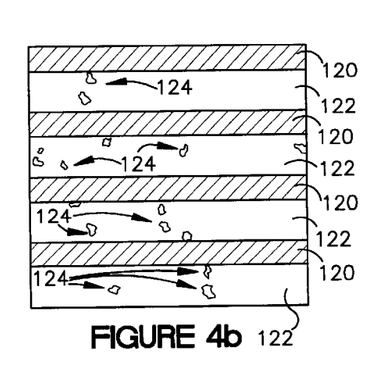
Figure 4C:
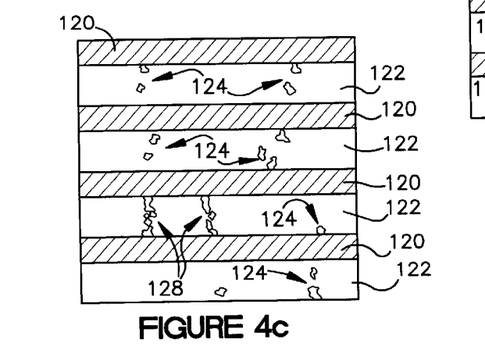

The formation of the bridge of wear-particles may be seen more clearly in conjunction with FIGS. 4a–4c. In FIG. 4a, a plurality of interdigitated electrodes 120 is formed on a substrate 122 and immersed in the fluid sample. An initial voltage is applied across the electrodes 120 and, as seen in FIG. 4a, various wear-particles 124 are not substantially influenced by the electric fields between the electrodes 120 because the electric field intensity is too small. In FIG. 4b, a larger voltage is applied to the electrodes 120, thus resulting in a stronger electric field intensity between the various electrodes 120. Note that the wear-particles 124 experience greater forces thereon due to the electric field and begin to align at various regions 126. The electric field in FIG. 4b, however, is not sufficiently strong to fully align the wear-particles 124 to thereby form a bridge between the electrodes. In FIG. 4c, the applied voltage across the electrodes 120 is equal to or greater than the critical voltage and the resulting electric field intensity is large enough to align fully some of the wear-particles 124 to form a bridge 128 between the electrodes 120. As discussed supra, the formation of the bridge 128 is detected by an increase in the current between the electrodes 120 since the bridge 128 reduces the resistance therebetween.

Figure 5:
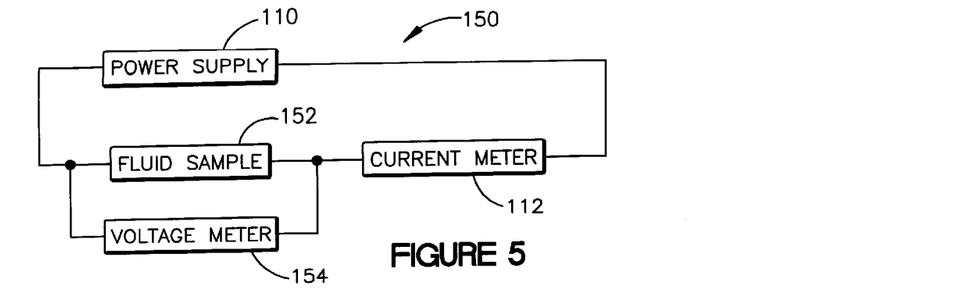
FIG. 5 is a block diagram illustrating a fluid sample test set-up according to the present invention.

A preferred test set-up 150 for verifying the electrogravity phenomena is illustrated in FIG. 5. The test set-up 150 includes a fluid sample 152 containing a sensor therein having spaced apart electrodes, with a voltage meter 154 applied directly across the fluid sample to thereby accurately measure the voltage across the electrodes therein. The current meter 112, as in FIG. 2, is then connected in series with the power supply 110. The power supply 110 is operable to provide a variable DC voltage between about 0–1,000 volts, however, this may vary depending upon the spacing of the electrodes. The current meter 112 provides a measurement of the current conducting through the electrodes. Therefore the set-up 150 of FIG. 5 allows for an accurate identification of the critical voltage at which a bridge forms between the electrodes.

Figure 6:
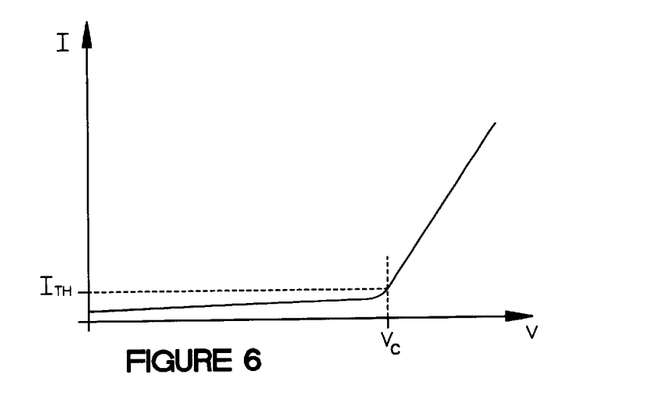
FIG. 6 is a graph illustrating an I/V curve associated with a fluid sample generated using the test set-up of FIG. 5, wherein a critical voltage is reached at a point where the current through the electrodes exceeds a predetermined threshold value.

As discussed above, at the critical voltage, one or more bridges 128 form between the electrodes and the current increases therebetween. A graphical illustration of the electrogravity phenomena is illustrated in FIG. 6. At applied voltages less than the critical voltage ($V_c$), the current does not change greatly and is below a threshold current level ($I_{TH}$). Therefore the slope of the I/V curve at applied voltages less than $V_C$ represents the conductivity (I/R) of the fluid sample. Similarly, the slope of the I/V curve at applied voltages which are equal to or greater than the critical voltage represents the conductivity (I/R) of the bridge of wear-particles which forms across the electrodes. The critical voltage ($V_c$) can thus be thought of in a graphical sense as a breakdown voltage since it is the value at the "knee" of the I/V curve of FIG. 6.

In order to experimentally verify in a more rigorous manner the preliminary results discussed above, the preferred experimental test set-up 150 of FIG. 5 was used and substrates 108 containing electrodes 106 spaced apart about 200 microns were immersed into various samples of mineral oil containing varying amounts of iron contaminants. The immersion depth "d" was also varied from about 1 cm to about 4 cm and the settling times were also varied between about 20 seconds to about 200 seconds. In each test sample, the applied voltage was varied between about 0 volts to about 500 volts within a rise time of about 20 seconds. The results of a number of the tests are illustrated in FIGS. 7a–7d. The multiple data points at a given oil depth relates to repeated experiments and the 500 volt readings do not necessarily reflect an actual measured critical voltage, but rather indicate the maximum voltage of the power supply 110 (therefore, the actual critical voltage would appear to be greater than 500 volts).

A theoretical and quantitative analysis was also conducted in order to investigate the impact of the settling time on the critical voltage measurements and to verify whether the experimental findings agreed with a theoretical analysis. Without application of a voltage across the electrodes, the settling of the wear-particles in the fluid due to gravity will not form a blanket layer or a bridge of conductive particles across the electrodes because the contaminant concentration levels are too low, however, as the wear-particles settle under the influence of gravity, a Poisson particle distribution is expected. The substrate 108 was divided into a number of small cells (i.e., about 200 micron×200 micron squares) that fit within the 200 micron electrode spacing. Since the wear-particles are each about 60 microns large in this particular analysis, at least four such wear-particles are required in order for a bridge of wear-particles to form in one of the cells. The wear-particles settle over the electrodes at a terminal velocity according to Stoke's law, however, additional particles accumulate along the edge of the electrodes due to the existence of an electric field, thus providing the possibility that only three wear-particles are needed to form the bridge. A result of the Poisson analysis for the different critical numbers of wear-particles required to form a bridge is illustrated below in Table 1.

TABLE 1

Prediction of Minimal Sample Depth and Falling Time

|  | 3 Particles | 3 Particles | 4 Particles | 4 Particles |
| --- | --- | --- | --- | --- |
| 1000 ppm ("d") | 0.33 cm (1 cell) | 0.42 cm (2 cells) | 0.81 cm (1 cell) | 0.97 cm (2 cells) |
| 1000 ppm ("t") | 24.6 seconds | 31.2 seconds | 59.4 seconds | 71.5 seconds |
| 200 ppm ("d") | 1.7 cm | 2.1 cm | 4.0 cm | 4.9 cm |
| 200 ppm ("t") | 123 seconds | 156 seconds | 297 seconds | 358 seconds |

Figure 8:
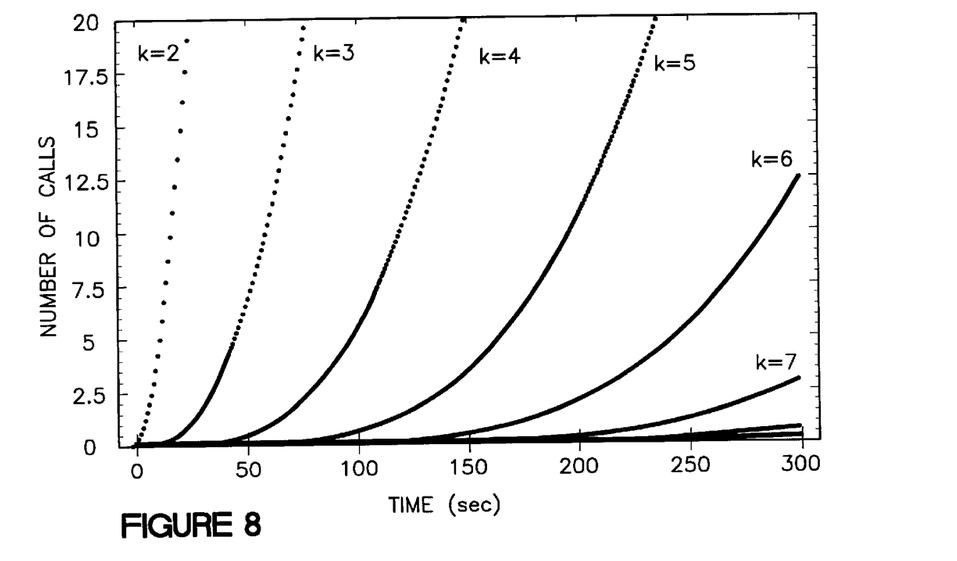
FIG. 8 is a graph illustrating the number of particles in various cells associated with the electrodes over a plurality of settling times.

The above Poisson analysis in Table 1 was confirmed experimentally, as illustrated in FIG. 8. FIG. 8 illustrates a set of curves showing the number of cells (200 micron×200 micron blocks) containing "k" wear-particles over time. FIG. 8 shows that as time increases, the number of cells containing "k" wear-particles increases.

Figure 7A:
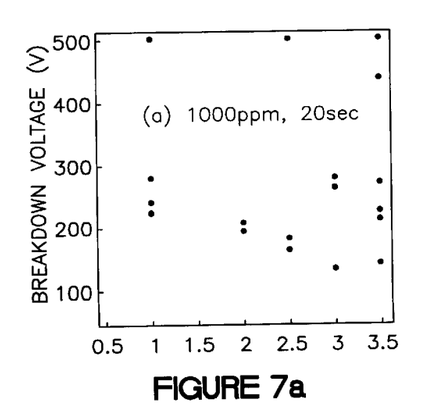
FIGS. 7a–7d are graphs illustrating experimental data taken with sample fluids having differing fluid contamination levels and measured at differing settling times which confirm the electrogravity phenomena and demonstrate a correlation between a critical voltage and a particulate contamination level within a sample fluid.
Figure 7B:
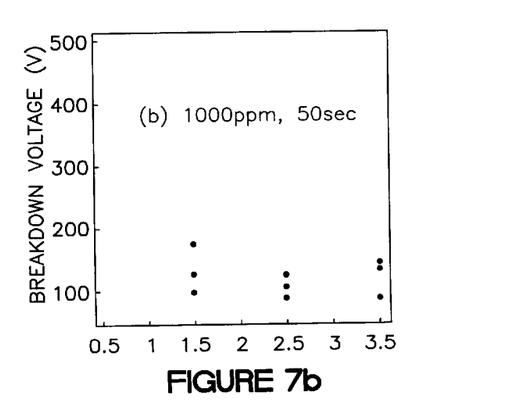
Figure 7C:
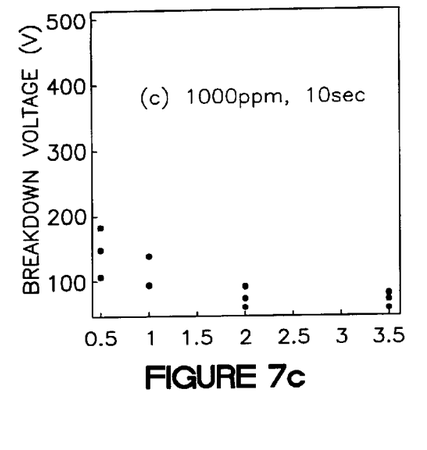
Figure 7D:
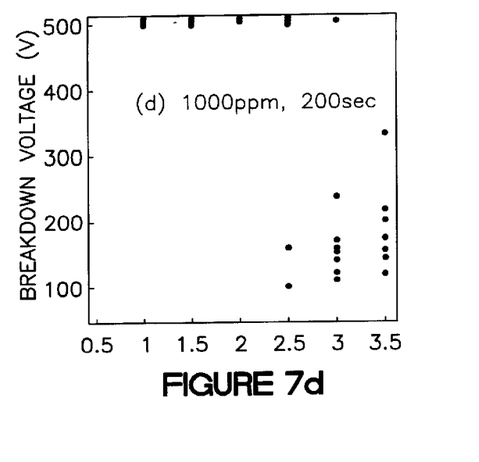

In bringing all the collected data and quantitative analysis together, the following conclusions can be drawn. First, for the 1000 ppm experiments, the critical voltage was observed at depths and waiting times that are consistent with Table 1 (e.g., the average settling time required for bridge formation at a given concentration correlated within a factor of two with the Poisson estimates). In addition, for the 200 ppm samples, bridge formation was not detected in settling times less than 100 seconds or when the depth of a fluid sample was shallower than 2.1 cm, which is consistent with the quantitative simulation in Table 1. Second, the large scatter of data points in FIG. 7a is a function of the short settling time. Although the concentration is large in FIG. 7a (i.e., 1000 ppm), the effect of the electric field in attracting additional, nearby particles to a particular cell is a bigger factor when gravity has not had time to settle the critical number of wear-particles for formation of a bridge. This same explanation applied to the data scattering found in the lower concentration sample of FIG. 7d when the depth is greater than 2.5 cm.

The third, and perhaps the most relevant conclusion from the above data, is that when two samples with different concentrations, but with the same settling time and the same sample depth "d" are tested, the lower wear-particle concentration sample requires a higher critical voltage to form a bridge between the electrodes. Therefore the critical voltage value is related to and correlates with the wear-particle concentration in a fluid sample. Lastly, it was appreciated that the Poisson analysis results assumed a constant wear-particle size. When the wear-particles used in the experimental tests were microscopically analyzed, however, it was determined that the 60 micron powder used to generate the fluid test samples exhibited a substantial size distribution between 10–70 microns which further helps understand the experimental data scatter.

Given the above discovery of the electrogravity phenomena and the discovery that the measured critical voltage correlates with the concentration of wear-particles in the fluid, the present invention is directed to a method and system of determining a particulate or wear-particle contamination level in a fluid.

Figure 9:
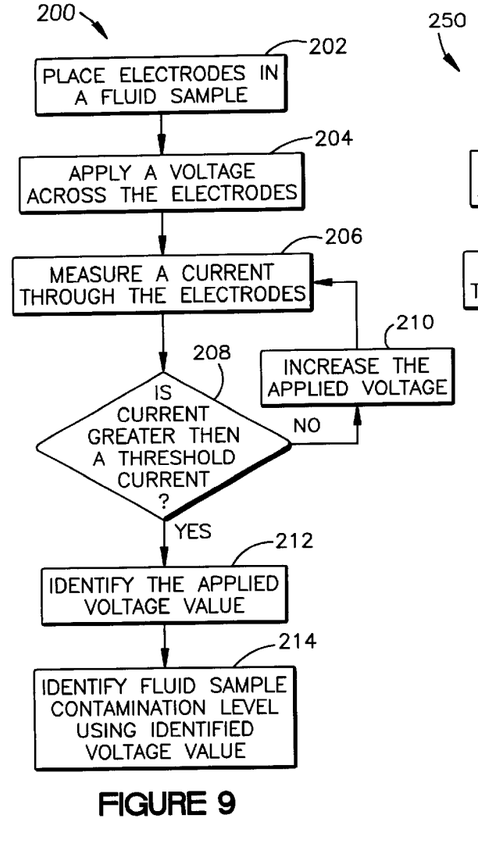
FIG. 9 is a flow chart diagram illustrating a method of detecting a particulate or wear-particle contamination level in a fluid sample according to the present invention.

A method 200 for determining the particulate contamination level is illustrated in FIG. 9. The method 200 begins by placing a pair of spaced apart electrodes within a fluid sample at step 202. Preferably, the electrodes are fixed onto a substrate, as illustrated in FIG. 2, however, such a sensor assembly is not required and the electrodes may be free-standing in the fluid. Any manner of bringing the fluid sample into contact with the electrodes is contemplated as falling within the scope of the present invention. Preferably at step 202, the electrodes are placed within the fluid sample at a predetermined depth, although various arbitrary depths may alternatively be used. If an arbitrary depth is used, it is preferable that the depth at which the electrodes reside in the fluid be identified and used in the subsequent fluid contamination concentration determination.

The method 200 continues at step 204, wherein a voltage is applied across the electrodes. Preferably, the voltage is applied using a DC type, variable power supply, however, various types of apparatuses and circuits may be utilized, for example, a voltage divider circuit having a plurality of outputs corresponding to differing voltage values with a multiplexer-type control switching circuit may be employed. Any manner of applying a voltage to the electrodes is contemplated as falling within the scope of the present invention. The initial voltage value is preferably a low voltage value in which the electric field will be insufficient to form a wear-particle bridge for reasons that will become clear below. Preferably, the application of the initial voltage occurs at a predetermined amount of time after the electrodes have been placed in the fluid sample in order to allow for sufficient settling of particulates. For example, settling times may vary between about 20–500 seconds and more preferably is about 50 seconds.

The current flowing through the electrodes is then measured at step 206. Preferably, such a measurement is conducted with a current meter, however, various current detection circuits may also be utilized. Any current detection methodology may be used and is contemplated as failing within the scope of the present invention. Once the current through the electrodes is measured, a determination is made at step 208 whether the magnitude of the current is greater than a predetermined current threshold value ($I_{TH}$). Preferably, the predetermined value is a current value that indicates that the resistance between the electrodes is no longer due solely to the resistance of the fluid sample, for example, a current value near the "knee" of the I/V curve of FIG. 6. Consequently, the current threshold preferably is a function of the conductivity of the fluid being analyzed.

According to an alternative embodiment of the present invention, step 208 may include a determination of whether the rate of change of current has increased above a predetermined threshold (i.e., whether the slope of the I/V has increased above a predetermined slope). In any event, step 208 is directed toward using the measured current through the electrodes in order to identify when the wear-particle bridge has formed and any manner of making such a determination using the measured current is contemplated as falling within the scope of the present invention.

If at step 208 a determination is made that the current does not exceed the predetermined threshold (NO), the applied voltage across the electrodes is incrementally increased at step 210. The current through the electrodes is then measured again at step 206 and steps 206, 208 and 210 are repeated until a determination is made at step 208 that the measured current exceeds the predetermined threshold value (YES).

Once the determination at step 208 is YES, the method 200 continues at step 212, wherein the applied voltage at which the current exceeds the threshold is identified as the critical voltage ($V_c$) since the current value corresponds to the change in resistance between the electrodes due to the formation of a wear-particle bridge between the electrodes. The manner in which the critical voltage is identified at step 212 can be achieved in a variety of different ways and any manner of doing so is contemplated as falling within the scope of the present invention. For example, one may simply take a visual reading of the power supply voltage when the current exceeds the predetermined threshold, or the data may be automatically recorded and stored in a memory. In another alternative embodiment, a separate voltage meter may be placed directly across the electrode or a voltage detection circuit may be coupled thereto to ensure that the critical voltage is measured accurately.

Once the critical voltage has been identified at step 212, the method 200 continues at step 214 by using the critical voltage value to determine the fluid sample contamination level. Preferably, the contamination level is determined by using a look up table which is constructed experimentally by using the above described electrogravity experimental set-up 150 of FIG. 5 with fluids having known contamination levels. Alternatively, using such data, an algorithm may be devised using, for example, a curve-fitting technique, to calculate the contamination level using the identified critical voltage. It is understood that in light of the above-described phenomena, a variety of different techniques may be employed and any such technique is contemplated as falling within the scope of the present invention.

As described above in conjunction with the method 200 of FIG. 9, the electrogravity phenomena is used according to the present invention to determine the actual contamination level of wear-particles in a sample fluid. Alternatively, the present invention also includes the use of the electrogravity phenomena to verify whether a particular fluid meets a particular purity level without indicating the exact contamination level. For example, for internal combustion engines, it is desirable for wear-particle concentration levels in the oil to be less than 50 ppm. Using the experimental test set-up 150 of FIG. 5, a fluid sample having a known wear-particle concentration level of 50 ppm may be tested to determine the critical voltage associated with the 50 ppm fluid contamination level. Such critical voltage information may then be used to give a pass/fail type output determination for a subsequent unknown test fluid. Such a method 250 is illustrated in FIG. 10.

Figure 10:
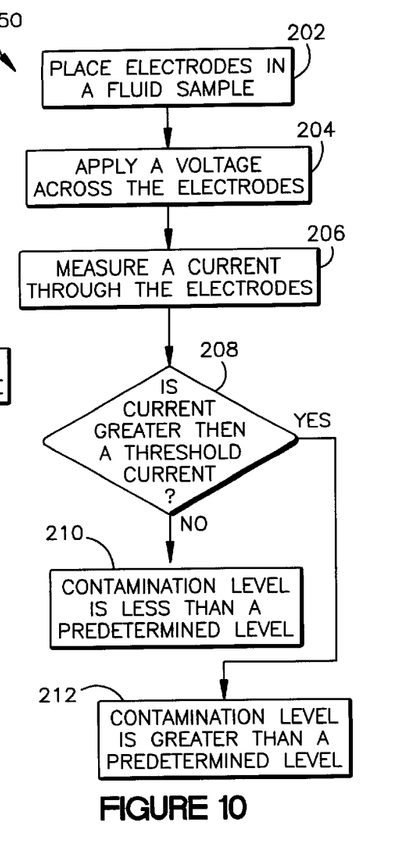
FIG. 10 is a flow chart diagram illustrating a method of determining whether a particular particulate contamination level exists within a fluid sample according to the present invention.

In FIG. 10, the method 250 proceeds initially in a manner which is similar to FIG. 9. Namely, the electrodes are preferably immersed in the unknown fluid (step 202), a voltage is applied to the electrodes (step 204), the current between the electrodes is measured (step 206) and a determination is made whether the measured current exceeds the predetermined threshold value (step 208). The applied voltage, at step 204, however, is preferably not an arbitrary voltage value, but rather is equal to or slightly greater than the critical voltage associated with a fluid having a 50 ppm wear-particle concentration. If the measured current value does not exceed the threshold current at step 208 (NO), then it is determined that the fluid does not have a contamination level which exceeds the 50 ppm concentration level and the fluid "passes" the test. If, however, the measured current does exceed the threshold current at step 208 (YES), then a wear-particle bridge did form at the applied voltage value; therefore a determination is made at step 212 that the contamination level of the unknown sample fluid is greater than 50 ppm (i.e., the fluid "fails" the test). Therefore, although the method 250 does not indicate the exact wear-particle concentration level in the fluid, the method 250 does provide a pass/fail indication with regards to a predetermined test contamination level (e.g., the fluid has a level greater than 50 ppm or a level less than 50 ppm). In the present exemplary embodiment of the present invention, a 100 ppm test contamination level was used and the applied voltage at step 204 was associated with that concentration level. In addition, the method 250 is equally applicable to other contamination levels and it is understood that the value of the applied voltage would correspondingly differ in order to be equal to or slightly greater than the critical voltage associated with the wear-particle concentration level of interest.

Figure 11:
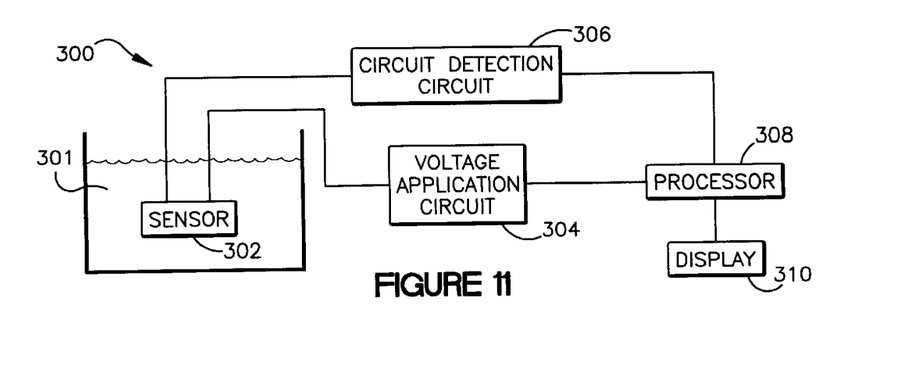
FIG. 11 is a system for analyzing a fluid sample and determining a particulate or wear-particle contamination level therein according to the present invention.

A system 300 for determining a wear-particle concentration level in a sample fluid 301 is disclosed in FIG. 11. The system 300 includes a sensor 302 which contacts the sample fluid 301. The sensor 302 is in electrical communication with (preferably physically coupled) a voltage application circuit 304 and a current detection circuit 306, respectively. The circuits 304 and 306 are in turn coupled to a processor 308, for example, as illustrated in FIG. 11, and the processor 308 is coupled to a display 310.

According to an exemplary embodiment of the present invention, the sensor 302 includes at least one pair of spaced apart electrodes attached to a substrate, for example, as illustrated in FIG. 2. Alternatively, the electrodes may maintain a spacing therebetween via use of a variety of spacing mechanisms and any such sensor construction which brings the electrodes into contact with the fluid sample is contemplated as falling within the scope of the present invention. Preferably, the system 300 includes a means for positioning the senor 302 within the fluid 301 at a predetermined depth or at a plurality of predetermined depths. For example, such means may include a graduated clip (not shown) which attaches to the container which holds the fluid 301 or a variable height pedestal may be placed under the sensor 302 in the container to obtain the predetermined depth. Any such mechanism may be used and is contemplated as falling within the scope of the present invention.

According to a preferred embodiment of the present invention, the voltage application circuit 304 and the current detection circuit 306 are controlled by the processor 308. Therefore according to the programming within the processor 308, the processor 308 controls the timing of the activation of the voltage application circuit 304, the voltage value which the circuit 304 applies, and the rate at which the applied voltage is varied. In addition, the processor 308 is operable to control the current detection circuit 306, for example, the timing at which the current is measured to coincide substantially with the activation timing of the voltage application circuit 304. For example, if the processor 308 activates the voltage application circuit 304 at time $t_1$, the processor 308 may wait until time $t_2$ to activate or read the output of the current detection circuit 306, wherein $t_2-t_1$ is a time interval which is sufficiently long to ensure a stable and accurate current measurement.

The processor 308 also provides output data to the display 310 to provide output data relating to the fluid test in a variety of data formats. For example, the processor 308 may output the data in the form of a graph similar to FIG. 6, wherein a user may visually see the "knee" of the I/V curve and identify or verify the critical voltage identification along with the wear-particle concentration level. Alternatively, the output data may include solely the identified critical voltage along with the determined wear-particle concentration level. In addition, the processor 308 may be interface through an I/O port (not shown) to customize the content and format of the output data. Although the display 310 is the preferred output peripheral, other peripherals may be used, for example, a printer, storage medium, etc.

The voltage application circuit 304 is preferably a variable DC power supply which may be controlled by the processor 308. Alternatively, the circuit 304 may be a variable DC supply with manual controls, as may be desired. The circuit 304 may also consist of other forms of voltage sources. For example, the circuit 304 may be a tunable voltage regulator circuit or a voltage divider circuit having a plurality of outputs for providing differing discrete voltage values. Any form of voltage generating or maintaining circuitry may be used and such circuit or circuits are contemplated as falling within the scope of the present invention. In addition, the voltage application circuit 304 is preferably coupled directly across the electrodes in the sensor 302. Alternatively, the circuit 304 may be coupled to one of the electrodes while the second electrode is grounded which will provide approximately the same voltage application accuracy provided the various grounds do not vary substantially.

The current detection circuit 306 is preferably a current meter in series with one of the electrodes, however, any type of current detection device or circuit may be used and is contemplated as falling within the scope of the present invention.

In operation, the processor 308 determines that the sensor 302 has been placed within the fluid sample. Preferably, the processor 308 waits a predetermined period of time, according to the desired settling time which is programmed therein. After the settling time has elapsed, the processor 308 preferably activates the voltage application circuit 304 at an initial voltage level, preferably a voltage which will be less than a critical voltage of the sample (e.g., 0 volts). For each voltage value which is applied to the electrodes in the sensor 302, the processor 308 then either activates the current detection circuit 306 or reads the measured current if the circuit 306 is passive and saves the data pair (i.e., the applied voltage and the measured current) in a memory associated therewith. In conjunction with saving the data pair, the processor 308 compares the measured current to a predetermined current threshold which resides in a memory associated with the processor 308 according to its programming and discontinues the process if the measured current exceeds the threshold current value and continues the process if the current is less than the threshold. The processor 308 then increases the applied voltage a predetermined amount within a predetermined period of time as dictated by its internal programming (e.g., the voltage step and rise time) and repeats the process of measuring the current at the new applied voltage value, saving the data pair and comparing the measured current to the predetermined current threshold. The processor 308 then continues the process until the measured current exceeds the threshold current value, at which point the data pair is saved and the applied voltage is identified as the critical voltage for that particular fluid 301. If the user wants a graphical output such as that illustrated in FIG. 6, however, the processor 308 continues increasing the applied voltage value and measures the current to establish the full graph; otherwise, the processor 308 deactivates the voltage application circuit 304.

According to another alternative embodiment of the present invention, the system 300 may use the measured current in a different manner in order to identify the critical voltage. For example, the processor 308 may use the collected data pair along with the previously collected data pair to calculate the slope of the conductivity between the electrodes for each applied voltage ($1/R=\Delta I/\Delta V$). When the processor 308 determines that a change in conductivity is greater than a predetermined amount, then the "knee" of the I/V curve has been identified and the critical voltage may be identified accordingly. In addition, the processor 308 may be programmed to identify the critical voltage using other techniques and any such programming to provide such functionality is contemplated as falling within the scope of the present invention.

Once the critical voltage has been identified for the fluid 301, the processor 308 uses the critical voltage value to determine the wear-particle concentration level for the fluid 301. Preferably, the processor 308 determines the concentration level by accessing a look up table in an associated memory which maps various critical voltage values (identified, for example, by earlier experimentation) to a particular concentration level for a given fluid depth and settling time. Alternatively, the processor 308 may calculate the concentration level using a programmed algorithm which accurately correlates the two parameters together. Any other type of programming of the processor 308 to determine the wear-particle concentration of the fluid 301 may be used and each is contemplated as falling within the scope of the present invention.

It is understood that for varying concentrations or varying wear-particle sizes, various parameters may be adjusted to accommodate the particular detection scheme or methodology. For example, the range of applied voltage may preferably be increased for small wear-particle sizes or for very low wear-particle concentrations because a greater electric field may be desirable to establish the wear-particle bridge. In addition, as discussed supra, the settling time and the electrode depth may be varied as desired or as needed. Further, the distance between the electrodes, the thickness of the electrodes and the number of electrodes may be varied. For example, if the wear-particle size is large, the distance between the electrodes may be increased to ensure that any reduced resistance therebetween is attributable to a wear-particle bridge as opposed to the random settling due to gravity of one or two wear-particles. Further still, the ramp time (i.e., the slope) of the applied voltage may be varied as appropriate. For example, if the accuracy of the correlation between the critical voltage and the wear-particle concentration is strongly dependent on the settling time, the slope or rate of change of the applied voltage is preferably large to collect all the data within a relatively short period of time so that all the collected data points are made at approximately the same settling time. Further still, the settling time may be varied based upon the fluid viscosity. For example, if the fluid has a high viscosity, the settling time may be increased. It is appreciated that each of the above variables may be altered to customize various wear-particle test schemes or methodologies and such variations are contemplated as falling within the scope of the present invention.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method of detecting wear-particle contamination in a fluid sample, comprising the steps of:

bringing the fluid sample into contact with a pair of spaced apart electrodes;

applying a voltage across the pair of spaced apart electrodes;

measuring a current between the electrodes; and determining whether a predetermined contamination level exists within the fluid sample based on the measured current;

wherein said determining step comprises identifying the current at which there is an electric field having an electrostatic force which is sufficient to substantially align some of the wear-particle contaminants in the fluid between the electrodes and thereby form a bridge between the electrodes.

2. The method of claim 1, wherein the spaced apart electrodes comprise interdigitated electrodes formed on a substrate.

3. The method of claim 1, wherein the applied voltage is a DC voltage having a value substantially equal to a critical voltage associated with the predetermined contamination level.

4. The method of claim 1, wherein applying the voltage across the electrodes comprise coupling a variable DC power supply across the electrodes to thereby generate a potential difference and thus an electric field therebetween.

5. The method of claim 1, wherein applying a voltage across the electrodes comprises applying a time-varying voltage across the electrodes, wherein the time-varying voltage is a substantially linear function of time.

6. The method of claim 1, wherein determining whether a contamination level exists comprises the steps of:

comparing the current to a predetermined current threshold; and determining that the contamination level exists within the fluid sample if the current exceeds the predetermined current threshold.

7. The method of claim 6, wherein the predetermined current threshold is related to a point in a current versus voltage curve for the predetermined contamination level where a slope changes from a low value to a high value, thus indicating a substantial change in conductivity between the electrodes.

8. A method of detecting wear-particle contamination in a fluid sample, comprising the steps of:

bringing a fluid sample into contact with a pair of spaced apart electrodes;

applying a plurality of voltages across the electrodes, wherein the plurality of voltages vary in magnitude between a first and second voltage level;

measuring a current between the electrodes at the plurality of voltages; and determining a wear-particle contamination level in the fluid sample using the measured currents;

wherein said determining step comprises identifying the current at which there is an electric field having an electrostatic force which is sufficient to substantially align some of the wear-particle contaminants in the fluid between the electrodes and thereby form a bridge between the electrodes.

9. The method of claim 8, wherein bringing the fluid sample into contact with the electrodes comprises the steps of:

forming the electrodes on a substrate; and placing the fluid sample over the substrate, thereby substantially immersing the electrodes within the fluid sample.

10. The method of claim 8, wherein applying the plurality of voltages across the electrodes comprises the steps of:

coupling a variable, DC power supply to the electrodes; and varying the power supply over time to thereby provide the differing applied voltages.

11. The method of claim 8, wherein the first voltage level is zero volts and the second voltage level is greater than a critical voltage at which a substantial increase in current will occur between the electrodes.

12. The method of claim 8, wherein measuring a current in the fluid sample comprises coupling a current meter in series with one of the electrodes and reading the current meter at the plurality of applied voltages.

13. The method of claim 8, wherein determining the wear-particle contamination level comprises the steps of:

identifying a critical voltage using the plot of measured currents; and correlating the identified critical voltage to the contamination level.

14. The method of claim 13, wherein the critical voltage corresponds to a voltage value which produces an electric field between the electrodes, and wherein an electrostatic force associated with the electric field is sufficient to substantially align a plurality of wear-particle contaminants within the fluid to form a bridge between the electrodes, and wherein the bridge substantially reduces a resistance between the electrodes.

15. The method of claim 13, wherein identifying the critical voltage comprises the steps of:

plotting the measured currents for each of the applied voltages;

calculating a slope at multiple points along the plot of measured currents; and selecting the applied voltage value at which the slope exceeds a predetermined value as the critical voltage.

16. The method of claim 13, wherein identifying the critical voltage comprises the steps of:

comparing the measured currents to a predetermined threshold; and identifying the lowest applied voltage which produced a current that exceeds the predetermined threshold.

17. The method of claim 8, wherein bringing a fluid sample into contact with the electrodes comprises the steps of:

forming the electrodes on a substrate;

placing the substrate within a container; and filling at least a portion of the container with the fluid sample, wherein the fluid sample covers the electrodes.

18. The method of claim 17, further comprising the step of waiting a predetermined period of time before applying the voltages and measuring the current in the fluid sample, wherein the predetermined period of time is sufficient to allow gravity to cause a settling of some of the contaminants in the fluid near the electrodes.

19. A system for determining a wear-particle contamination level in a fluid sample, comprising:
- a sensor including a pair of spaced apart electrodes, wherein the fluid sample is brought into contact with the electrodes for detection of the level of wear-particle contamination therein;
- a voltage application circuit for applying a voltage across the spaced apart electrodes; and
- a current sensor coupled to one of the electrodes, wherein the current sensor measures a current magnitude between the electrodes, and wherein the current magnitude is associated with the particulate contamination level in the fluid sample;
- a processor operably coupled to the current sensor and operable to identify the current at which there is an electric field having an electrostatic force which is sufficient to substantially align some of the wear-particle contaminants in the fluid between the electrodes to and thereby form a bridge between the electrodes.

20. The system of claim 19, wherein the processor is also coupled to the voltage application circuit, and wherein the processor is operable to control a magnitude of the applied voltage provided by the voltage application circuit and is further operable to compare the current magnitude to a predetermined threshold and identify the lowest applied voltage at which the current magnitude exceeds the predetermined threshold.

21. The system of claim 20, wherein the processor determines the particulate contamination level in the fluid sample using the value of the lowest applied voltage at which the current magnitude exceeds the predetermined threshold.

22. The system of claim 21, wherein the processor determines the particulate contamination level in the fluid sample, by one of calculating the particulate contamination level using the value of the applied voltage according to a programmed algorithm or determining the particulate contamination level using the value of the applied voltage in a look up table.

23. The system of claim 19, wherein the processor is also coupled to the voltage application circuit, and wherein the processor is operable to control a magnitude of the applied voltage provided by the voltage application circuit and is further operable to detect a rate of change of current between the electrodes and identify the applied voltage at which the rate of change of current exceeds a predetermined threshold.

24. The system of claim 20, further comprising a display coupled to the processor, wherein the display provides an illustration of one or more portions of output data associated with the fluid sample.

25. The system of claim 19, wherein the voltage application circuit comprises a variable power supply which is operable to apply a plurality of voltage values across the electrodes.

26. A method of detecting wear-particle contamination in a fluid, comprising the steps of:
- bringing a fluid sample having wear-particle contaminants therein into contact with a pair of spaced apart electrodes;
- applying a voltage across the pair of spaced apart electrodes, wherein the voltage generates an electric field between the electrodes, and wherein the electric field exerts an electrostatic force on the wear-particle contaminants;
- increasing the voltage to a critical voltage value, wherein the critical voltage value produces an electric field having an electrostatic force which is sufficient to substantially align some of the wear-particle contaminants in the fluid between the electrodes, thereby forming a bridge between the electrodes, and wherein the bridge of wear-particle contaminants substantially reduces the resistance between the electrodes; and
- correlating the critical voltage value to a wear-particle contamination level, thereby identifying the wear-particle contamination in the fluid.

27. A method of detecting wear-particle contamination in a fluid sample, comprising the steps of:
- applying a varying voltage across a fluid sample;
- determining a critical voltage at which there is a substantial change in conductivity of the fluid sample; and
- correlating the identified critical voltage to a contamination level.

28. A method of detecting wear-particle contamination in a fluid sample, comprising the steps of:
- bringing the fluid sample into contact with a pair of spaced apart electrodes;
- applying a voltage across the pair of spaced apart electrodes;
- measuring a current between the electrodes; and
- determining whether a predetermined contamination level exists within the fluid sample based on the measured current;
- wherein applying a voltage across the electrodes comprises applying a time-varying voltage across the electrodes and wherein the time-varying voltage is a substantially linear function of time.

29. A method of detecting wear-particle contamination in a fluid sample, comprising the steps of:
- bringing the fluid sample into contact with a pair of spaced apart electrodes;
- applying a voltage across the pair of spaced apart electrodes;
- measuring a current between the electrodes; and
- determining whether a predetermined contamination level exists within the fluid sample based on the measured current by comparing the current to a predetermined current threshold and determining that the contamination level exists within the fluid sample if the current exceeds the predetermined current threshold;
- wherein the predetermined current threshold is related to a point in a current versus voltage curve for the predetermined contamination level where a slope changes from a low value to a high value, thus indicating a substantial change in conductivity between the electrodes.

30. A method of detecting wear-particle contamination in a fluid sample, comprising the steps of:
- bringing a fluid sample into contact with a pair of spaced apart electrodes;
- applying a plurality of voltages across the electrodes, wherein the plurality of voltages vary in magnitude between a first and second voltage level;
- measuring a current between the electrodes at the plurality of voltages; and
- determining a wear-particle contamination level in the fluid sample using the measured currents;
- wherein the first voltage level is zero volts and the second voltage level is greater than a critical voltage at which a substantial increase in current will occur between the electrodes.

31. The method of claim 26, wherein the critical voltage value is related to a point in a current versus voltage curve where a slope changes from a low value to a high value, thus indicating a substantial change in conductivity between the electrodes.

32. A method of detecting contamination in a fluid sample, comprising the steps of:

determining a critical voltage which produces an electric field having an electrostatic force which is sufficient to substantially align contaminants in the fluid to form a bridge; and correlating the critical voltage to a contamination level.

* * * * *